United States Patent [19]

Silvian

[11] Patent Number: 4,979,506
[45] Date of Patent: Dec. 25, 1990

[54] SELF-TEST SYSTEM AND METHOD FOR EXTERNAL PROGRAMMING DEVICE

[75] Inventor: Sergiu Silvian, La Crescenta, Calif.

[73] Assignee: Siemens-Pacesetter, Inc., Sylmar, Calif.

[21] Appl. No.: 391,079

[22] Filed: Aug. 8, 1989

[51] Int. Cl.$^5$ .............................................. A61N 1/00
[52] U.S. Cl. ........................... 128/419 PT; 128/903; 128/419 PG; 340/825.69; 375/10; 371/16.4; 371/25.1; 371/20.3
[58] Field of Search .................. 128/419 PG, 419 PT, 128/419 PS, 903; 364/413.02–413.06; 375/10; 340/825.69, 825.72, 514; 371/15.1, 25.1, 16.4, 35.1, 27

[56] References Cited

U.S. PATENT DOCUMENTS

| | | | |
|---|---|---|---|
| 4,232,679 | 11/1980 | Schulman | 128/419 PG |
| 4,551,839 | 11/1985 | Botrel et al. | 371/35 |
| 4,712,179 | 12/1987 | Heimer | 128/903 |
| 4,799,220 | 1/1989 | Nielsen | 371/25.1 |
| 4,821,266 | 4/1989 | Ohm et al. | 371/25.1 |
| 4,823,344 | 4/1989 | Yonehara | 375/10 |
| 4,867,163 | 9/1989 | Schaldach | 128/419 PG |

*Primary Examiner*—Francis Jaworski
*Assistant Examiner*—George Manuel
*Attorney, Agent, or Firm*—Leslie S. Miller; Lisa P. Weinberg; Malcolm J. Romano

[57] ABSTRACT

A communication system includes self-test means for automatically testing its performance. The communication system is adapted for use between an implantable device, such as a pacemaker, and an external device, such as the pacemaker's programmer. The communication system includes in the external device a transmitter circuit for transmitting an output signal through an antenna, and a receiver circuit for receiving an input signal through an antenna. A driver circuit controls the operation of the transmitter circuit. A microprocessor, connected to the driver circuit, controls the information content and timing of the transmitted output signal. A bandpass filter and AM demodulator process the input signal received through the receiver circuit. A multiplexer selectively allows one of a plurality of status signals from throughout the communication system within the external device, including the demodulated signal obtained from the AM demodulator, to be connected to the microprocessor. The self-test means includes means for having the microprocessor generate a test signal that is selectively injected into the transmitter circuit and/or the bandpass filter. The self-test means further includes a switch that selectively allows, as controlled by the microprocessor, either the output signal from the bandpass filter, or the output signal from the transmitter circuit, to be connected to the input of the AM demodulator. In this manner, the injected test signal, or the effects of the injected test signal, may be coupled back to the microprocessor via one of the status signals. The microprocessor then checks the status signals to ensure that a desired performance criteria is achieved. Individual tests may be selectively performed, or a prescribed sequence of several tests may be automatically performed.

29 Claims, 3 Drawing Sheets

SELF-TEST SYSTEM AND METHOD FOR EXTERNAL PROGRAMMING DEVICE

BACKGROUND OF THE INVENTION

The present invention relates to testing systems and methods for verifying the operation of an external programming device used to monitor and control an implantable device, such as an implantable pacemaker. More particularly, the present invention relates to a self contained testing system and method that verifies the operation of the communication circuits within the external programming device that are used to establish a telemetry link with the implantable device.

Implantable devices are implanted in a human or animal for the purpose of performing a desired function. This function may be purely observational or experimental in nature, such as monitoring certain body functions; or it may be therapeutic or regulatory in nature, such as providing critical electrical stimulation pulses to certain body tissue, nerves or organs for the purpose of evoking a desired response. The modern implantable demand pacemaker is an example of an implantable device that performs both observational and regulatory functions, i.e., it monitors the heart to make sure it beats at an appropriate rate; and if not, it causes an electrical stimulation pulse to be delivered to the heart in an attempt to force the heart to beat at an appropriate rate.

In order for an implantable device to perform its functions at minimum inconvenience and risk to the person or animal within whom it is used, some sort of non-invasive telemetry means must be used to allow data and commands to be easily passed between the implantable device and an external device. Such external device, known by a variety of names, such as a controller, programmer, or monitor, will generally be referred to herein as an "external programming device", where "external" connotes non-implanted. The external programming device provides a convenient mechanism through which the operation of the implantable device can be controlled and monitored, and through which data sensed or detected by the implantable device can be transferred to the external programming device where it can be read, interpreted, or otherwise used in a constructive manner.

A commonly known implantable device is the implantable pacemaker. All known implantable pacemakers utilize a corresponding external programming device to control (program) and monitor their operation. While the present invention is not limited to the external programming devices used with implantable pacemakers, such external devices comprise the best presently known application for the present invention. The present invention can thus be better understood and appreciated if a basic understanding of such devices, i.e., implantable pacemakers and their corresponding external programmers, is also known. A description of a pacemaker, for example, including a description of some of the special features that may be included in a pacemaker, may be found, e.g., in U.S. Pat. Nos. 4,686,988, 4,712,555 and 4,788,980. Similarly, a description of a modern external programming device may be found in U.S. Pat. No. 4,809,697. A description of some of the different types of telemetry systems that may be used to establish a communication link between an implantable pacemaker and an external programming device may be found, e.g., in U.S. Pat. No. 4,681,111 and in applicant's copending patent application, "High Speed Digital Telemetry System For Implantable Device," Ser. No. 07/391,080, filed herewith. These patents and application are all assigned to the same assignee (or a related assignee) as is the present application, and are all incorporated herein by reference.

One of the difficulties associated with using an external programming device to monitor and control an implanted device is being able to quickly determine the source of a potential malfunction when such potential malfunction is detected. For example, if status data received from the implantable device indicates some circuit of the implantable device is not functioning properly, it must quickly be determined whether the circuit in the implantable device is, in fact, malfunctioning; or whether the telemetry circuits and data processing circuits within the external programming device have failed to present the data properly. Similarly, if a programming command is sent to the implantable device from the external programming device, but the programming device fails to respond to the command properly, a determination must be quickly made as to whether the correct command was in fact sent to the implantable device by the external programmer or whether something is in fact wrong with the implantable device.

Heretofore, determinations such as are described in the previous paragraph have required that special diagnostic tests be performed in an attempt to isolate the source of the problem. Besides taking a significant amount of time to perform, it is not uncommon for such diagnostic tests to require a thorough knowledge of how the pacemaker and external programmer operate, as well as the use of additional test equipment, such as multimeters, signal generators, oscilloscopes, and the like. Further, personnel trained in the use of such test equipment are also needed. Unfortunately, such additional test equipment and/or skilled personnel is not always readily available at the time a determination as to the source of a problem must be made. Moreover, even when a particular diagnostic test is performed, and the source of a potential problem is identified, the results of the test may not present sufficient data to allow the appropriate corrective action to be taken. Before such corrective action can be taken, it is not uncommon for very extensive and comprehensive tests to be made, requiring still more time, more test equipment, and technically skilled personnel to perform the tests. Hence, it is evident that what is needed is a comprehensive test that can be performed easily and rapidly to accurately determine the source of a potential malfunction, as well as appropriate corrective action, without requiring either special test equipment or technically skilled personnel. Such comprehensive tests could not only greatly facilitate diagnostic evaluation of implantable devices in actual use, i.e., devices implanted in patients, but could also be very useful during the manufacture and initial test of such devices at the manufacturing facility.

In the absence of technically trained personnel, there is also a problem when using implantable devices of knowing when a particular test should be performed. For example, in the case of implantable medical devices, where the proper operation of the implantable device, and its corresponding external programming device, may present a life-threatening situation, it may be preferable to check the performance of the external programming device on a periodic basis. A medical doctor or medical technician (who is highly trained medically, and is trained relative to how to use an external programming device, but may nonetheless lack the technical skills required to thoroughly understand the external programming device), may not know or appreciate when such periodic tests should be performed. Further, a medical doctor or medical technician, preoccupied with other more pressing concerns, may simply forget to perform periodic tests. What is needed, therefore, is a self-test that is built-in to the external programming device and that conducts certain key tests automatically at prescribed times during the operation of the device.

Another problem commonly encountered in the use of implantable devices is compatibility with the external programming device. It is not uncommon, for example, in the medical implantable device field (e.g., pacemakers) for a particular pacemaker manufacturer to have several models of pacemakers implanted in patients. Each pacemaker model may include a different type of telemetry system, requiring a different type of external programming device for use therewith. Hence, a doctor (or other medical personnel) may need several different models of external programming devices in order to properly monitor all of his or her patients, each of whom may have a different model pacemaker implanted in his or her body. Keeping track of which external programming device is to be used with which patient, as well as which tests should be performed on all the different models of external programming devices, may become quite burdensome. Hence, what is needed is a universal external programming device that can be used with all models of a particular manufacturer's implantable devices, and that includes self-test features built therein that automatically or selectively perform the appropriate tests at the appropriate times.

The present invention advantageously addresses the above and other needs.

SUMMARY OF THE INVENTION

The present invention is directed to a self-test system and method for testing the performance of an external programming device used to control and monitor the performance of an implantable device. While such a self-test system and method may be used in a wide variety of different applications, they are particularly well suited for use with an implantable medical device. This is because the operation of an implantable medical device, such as a pacemaker, must be regularly monitored and checked for a desired performance. Such monitoring is routinely done using an external programming device. However, in monitoring an implantable medical device with an external programming device, if a malfunction of some kind is indicated, it is imperative to quickly and reliably determine the source of the malfunction: the implantable device or the external programming device. The present invention quickly performs a self-test of the circuits, particularly the telemetry circuits, of the external programming device, thereby providing an indication as to the source of the malfunction.

The hardware used by the self-test system of the present invention may be totally self-contained within the external programming device, thus obviating the need for additional test equipment, such as signal generators or signal measuring devices (multimeters, oscilloscopes, and the like). Likewise, the method of self-testing taught by the present invention may be readily and, if desired, automatically carried out using such self-contained hardware as controlled by stored sequences of instructions, or equivalent programming means, stored within the external programming device. The execution of the self-tests thus requires no special equipment or operator skills, and may be readily carried out when necessary or desired.

Advantageously, the self-test system herein described provides for several different tests to be performed, thereby providing for the verification of all of the key functions of the external programming device. Such comprehensive verification not only allows for the quick identification of the source of a potential malfunction, but also aids in determining the proper corrective action that should be taken in response to the malfunction.

Further, in a preferred embodiment, the self-test system is invoked automatically at prescribed times during the operation of the communication system, providing a display of the self-test results only when one of the tests included in the self-test system indicates a test failure (malfunction). Hence, the absence of any display of test results indicates that the appropriate circuits within the external programming device are functioning properly. Thus, in operation, unless such test results are displayed, the user of the external programming device need not be concerned at all with performing any type of diagnostic or similar tests.

The communication (telemetry) system in an external programming device typically includes one or more transmitter circuits for transmitting an output signal to the implantable device through an antenna. (It is noted that multiple transmitter circuits may be employed, for example, where the external programming device is designed for use with more than one type of implantable device.) The external programming device further includes at least one receiver circuit for receiving an input signal from the implantable device through an antenna. A driver circuit controls the operation of the transmitter circuit. A microprocessor, or equivalent control circuit, connected to the driver circuit, controls the information content and timing of the transmitted output signal. A bandpass filter and AM demodulator process the input signal received through the receiver circuit. A multiplexer circuit selectively connects one of a plurality of status signals from throughout the circuits of the external programming device, including the demodulated signal obtained from the AM demodulator, to the microprocessor.

The self-test system of the present invention includes means for having the microprocessor, or equivalent circuit, generate a test signal that is selectively injected into the transmitter circuit and/or the bandpass filter. The self-test means further includes a switch that selectively allows, as controlled by the microprocessor, either the output signal from the bandpass filter, or the output signal from the transmitter circuit, to be connected to the input of the AM demodulator. In this manner, the injected test signal, or the effects of the injected test signal, may be coupled back to the microprocessor via one of the status signals. The microprocessor then checks the status signals to ensure that a desired performance criteria is achieved.

For example, to test the transmitter circuit, the microprocessor generates an appropriate test data word, e.g., several bits of a prescribed bit pattern, that is injected into the transmitter circuit. This test data word may be simply a square wave of a prescribed frequency. The output signal from the transmitter circuit, after being attenuated an appropriate amount (to simulate losses that occur in a typical communication channel) is then coupled into the demodulator circuit, where the test data word is demodulated. The demodulated output signal is then routed back to the microprocessor through the multiplexer circuit where it is checked for the proper data word. If the proper data word is received back at the microprocessor, then that serves as an indication that the transmitter circuit is functioning properly.

Similar tests are performed to test other circuits of the external programmer. These tests all involve generating a suitable test signal, injecting the test signal into the appropriate locations within the circuits of the programmer, and routing the resulting signals, obtained or derived from the output of particular circuit under test, back to a central location within the external programmer, such as the microprocessor, where the resulting signal is compared against the signal(s) that should be received if the particular circuit(s) under test is functioning properly.

Advantageously, the self-test system of the present invention allows individual tests to be selectively performed, or a prescribed sequence of several tests to be automatically performed.

In accordance with one embodiment, the self-test system of the present invention may be characterized as a system for testing an external programming device that includes: (a) test signal means for generating a test signal within the external programming device; (b) injection means for injecting the test signal into prescribed circuit locations within the external programming device; (c) monitoring means for monitoring prescribed signals, resulting from the injecting of the test signal, at prescribed circuit locations within the external programming device; and (d) comparison means for comparing the value of various parameters associated with the monitored signals with expected parameter values.

In accordance with another embodiment, the present invention may be characterized as self-test means for use with a communication system, where the communication system includes driver means for generating a first signal that is to be transmitted; transmitter means for presenting the first signal to an antenna as an output signal; control means for controlling the driver means; receiver means for receiving an input signal from an antenna and converting the same to a second signal; filter means for filtering the second signal and for producing a filtered second signal therefrom; demodulation means for demodulating the filtered second signal and for producing a demodulated signal therefrom; and first switch means for selectively connecting one of a plurality of status signals, including the demodulated signal, to the control means. The self-test means in accordance with this embodiment of the invention comprises: (a) signal generating means within the control means for generating a test signal; (b) first summing means for selectively adding the test signal to the first signal, thereby causing the output signal to selectively include the test signal; (c) second summing means for selectively adding the test signal to the second signal, thereby causing the filtered second signal to selectively include the test signal; and (d) second switch means for selectively connecting one of the output signal or the filtered second signal to the demodulation means, thereby causing one of the status signals connected to the control means to selectively include the test signal after the test signal has passed through the transmitter means and demodulator means or after the test signal has passed through the filter means and demodulation means. The control means includes means for checking the selected one of the status signals returned thereto to verify that the test signal produced an anticipated response in the performance of the communication system. If so, the self-test is considered as passed; if not, the self-test is considered as failed.

The present invention may further be characterized as a method for testing an external programming device that includes: (a) generating a test signal within the external programming device; (b) injecting the test signal into prescribed circuit locations within the external programming device; (c) monitoring prescribed signals, resulting from the injecting of the test signal, at prescribed circuit locations within the external programming device; and (d) comparing the value of various parameters associated with the monitored signals with expected parameter values.

Similarly, the present invention may be characterized as a method of automatically testing an external programming device comprising: (a) automatically performing a prescribed test at the time the external programming device is first powered on; (b) determining if the results of the test performed in step (a) are within a range of acceptable results; (c) automatically saving the results of the test performed in step (a) if the results of the test are not within the range of acceptable results as determined in step (b); (d) automatically repeating steps (a) through (c) for additional prescribed tests, if any, that are to be performed, with each additional test being initiated at the conclusion of the preceding test; and (e) automatically displaying the results of the tests saved in step (c) for all the prescribed tests that are performed. Advantageously, this method automatically performs a sequence of prescribed tests when the programming device is first powered on, with the results of any test not within an acceptable range of results being automatically displayed.

It is an aspect of the present invention to provide a system and method for quickly testing an external programming device used with an implantable device, thereby allowing a determination to be rapidly made as to whether a potential malfunction indicated by monitoring the implantable device with the external programming device is caused by the implantable device or the external programming device.

It is a further aspect of the present invention to provide versatile testing circuits that are self-contained within an external programming device, adapted for use with an implantable device, which testing circuits can advantageously be used both during the manufacture and initial test of the implantable device and external programming device, and during subsequent use of the implantable device after implant.

It is still another aspect of the invention to provide such self-contained testing circuits within an external programming device that are simple to use, requiring no additional test equipment or special skills of the operating personnel.

It is a still further aspect of the invention to provide such simple-to-use self-contained testing circuits that perform a wide range of comprehensive tests directed to all of the major circuits of the programming device.

It is yet another aspect of the invention to provide such self-contained testing circuits that may be programmed to automatically perform a desired sequence of tests at prescribed times during the operation of the external programming device, such as when the external programming device is first turned on. In accordance with this aspect of the invention, selected test results, such as results from a failed test, may be automatically saved for future reference and display.

It is also an aspect of the invention to provide a single, versatile, multimode external programming device having self-test capabilities that can be used with a wide variety of different types of implantable devices, such as several different models and versions of implantable pacemakers.

It is another aspect of the invention to provide a simple and fast method of testing the circuits of an external programmer to determine whether such circuits are performing properly.

BRIEF DESCRIPTION OF THE DRAWINGS

The above and other aspects, advantages and features of the present invention will be more apparent from the following more particular description thereof, presented in conjunction with the following drawings and appendix, wherein.

DETAILED DESCRIPTION OF THE INVENTION

The following description is of the best mode presently contemplated for practicing the invention. This description is not to be taken in a limiting sense but is made merely for the purpose of describing the general principles of the invention. The scope of the invention should be ascertained with reference to the issued claims.

In the description of the invention that follows, like numerals or reference designators will be used to refer to like parts or elements throughout.

Figures 1, 3, 4:
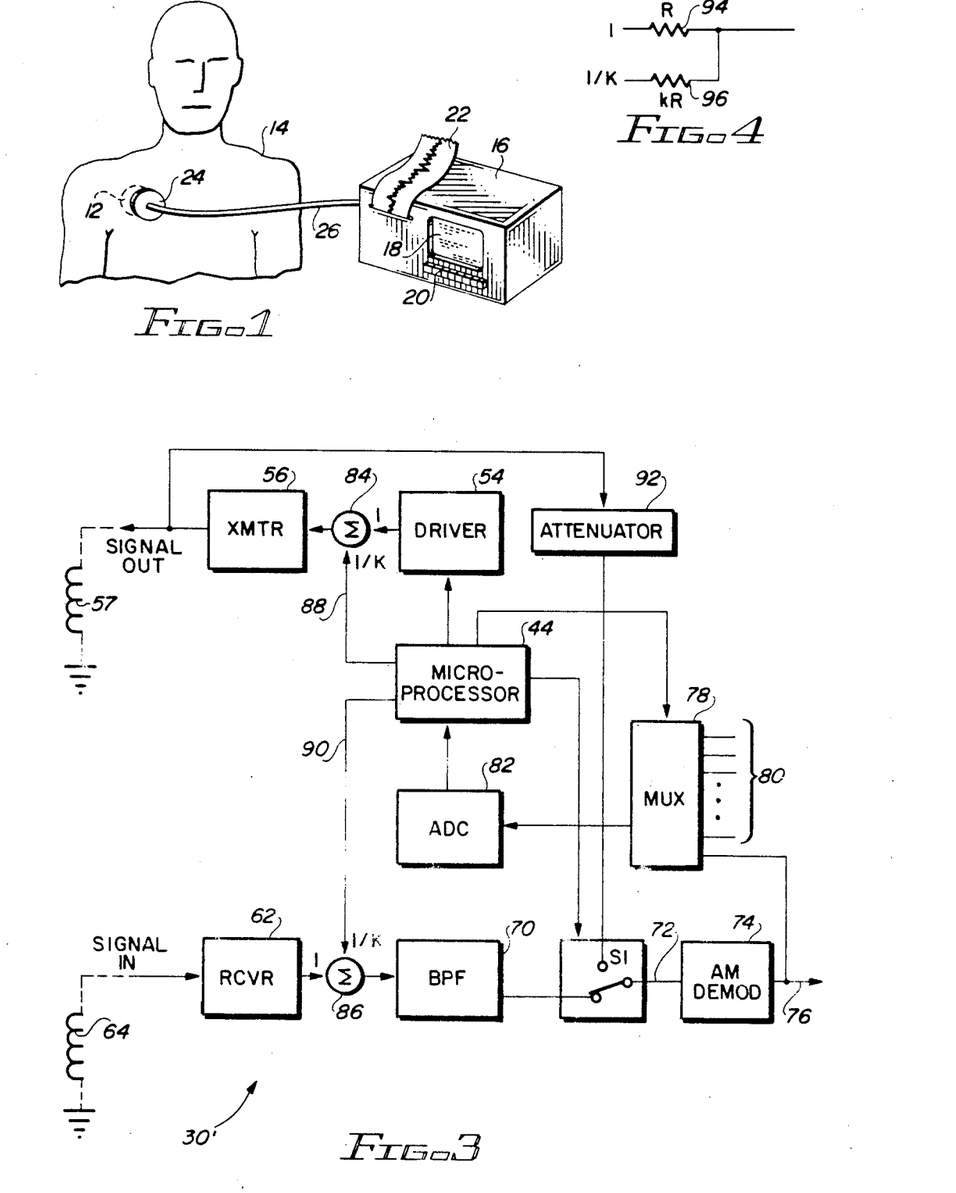
FIG. 1 diagrammatically shows an implanted pacemaker in a patient in communicative contact with an external programming device.
FIG. 3 is a block diagram similar to FIG. 2 and further shows the additional hardware elements of the self-test means of the present invention, including two summer circuits and a switch.
FIG. 4 is a schematic diagram of a preferred summer circuit used in FIG. 3.

FIG. 1 diagrammatically shows a representative implantable device, a pacemaker 12, implanted in a patient 14. The pacemaker 12 is shown in communicative contact with an external programming device 16. (It is noted that the present invention is not limited to pacemakers or programmers used with pacemakers, but applies to all implantable devices and their corresponding external programming devices). The external programming device 16 includes a display screen 18, control buttons or switches 20, and means for printing data or waveforms on a paper tape 22.

In use, a programming head 24, connected to the programmer 16 by way of a suitable cable 26, is positioned near (within a few inches) the implanted pacemaker 12. The programming head includes an antenna coil, shown below in FIGS. 2 and 3, that is inductively coupled, or otherwise electromagnetically linked, with a corresponding antenna coil in the pacemaker 12. This linkage advantageously allows commands to be sent to the implantable pacemaker 12 from the external programming device 16, as well as information from the pacemaker 12 to be sent to the external programming device 16. For example, the external programming device 16 may send the pacemaker 12 a command, selected by pushing an appropriate button or combination of buttons, that causes the pacemaker to operate in a particular mode, such as the VVI mode. The pacemaker 12 may send data to the programmer 16 that indicates its presently programmed mode of operation, the status of its internal batteries, and the cardiac activity sensed by its sensing circuits. The data and cardiac activity may advantageously be displayed on the display and/or printed on the paper tape 22. As indicated in the previously cited U.S. Pat. No. 4,809,697, the screen of the display 18 may include a touch sensitive overlay that permits the screen itself to function as additional buttons or keys that can be pressed by the user of the programmer in order to select different programming options.

Figure 2:
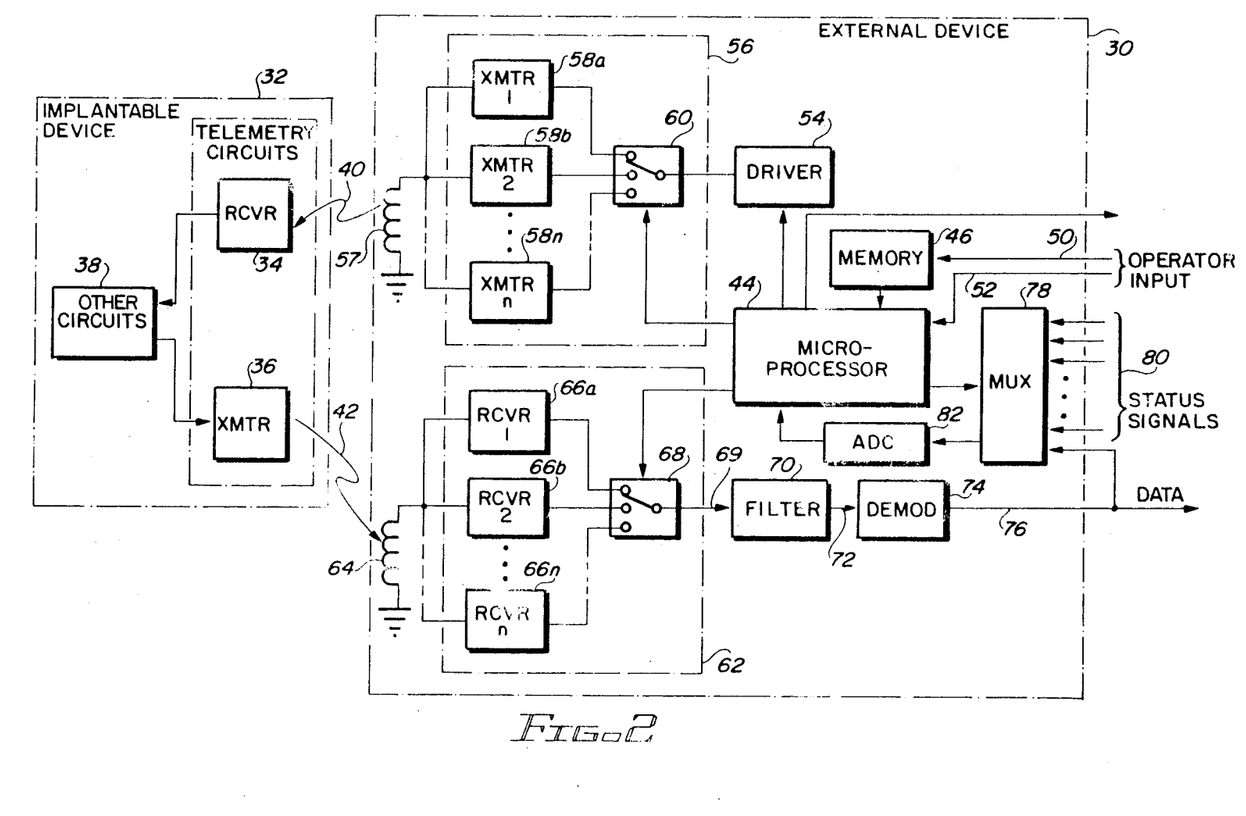
FIG. 2 is a block diagram of the communication circuits within an external programming device, which external programming device is adapted to interface with a plurality of different models and types of implantable devices.

Referring to FIG. 2, a block diagram of the communication (telemetry) circuits of a universal external programming device 30 and an implantable device 32 is shown. The telemetry circuits of the implantable device 32 include a receiver 34 and a transmitter 36. These circuits are coupled to the other circuits 38 of the implantable device. In operation, the receiver circuit 34 receives command signals transmitted from the external programming device 30, which command signals are symbolically depicted in FIG. 2 as a wavy line 40. The transmitter 36 transmits data signals to the external programming device 30, which data signals are symbolically depicted in FIG. 2 as a wavy line 42. Both the transmitter 36 and the receiver 34 of the implantable device 32 include an antenna coil, or equivalent, (not shown in FIG. 2) for receiving the signals 40 or sending the signals 42. In some models of implantable devices, the same antenna coil may be used for both sending and receiving. As the present invention relates to the operation and circuits within the external device 30, no further detail will be given herein concerning the circuits in the implantable device 30.

As shown in FIG. 2, the external programming device 30 (sometimes referred to hereafter as simply the "external device", the "programming device", or simply the "programmer") includes a microprocessor circuit 44 coupled to a suitable memory circuit 46. The memory circuit 46 has stored therein various stored sequences of instructions that cause the microprocessor to operate in a prescribed fashion. These stored instructions may be altered, as desired, by rewriting the contents of the memory 46 using an appropriate rewrite command sent to the memory 46 over signal line 50. Similarly, the operation of the microprocessor 44 may be manually altered (i.e., the stored sequence of instructions may be overridden) by sending an appropriate interrupt command thereto over signal line 52. It is noted that both the rewrite command and the interrupt command typically originate with the operator (user) of the eternal device 30. The operation of a microprocessor circuit, including the manner of programming a microprocessor circuit using a memory circuit, are well known in the art.

For sending commands to the implantable device 32, the external device 30 includes a driver circuit 54 coupled to a transmitting network 56. It is the function of the driver circuit 54 to generate the appropriate command words, as controlled by the microprocessor 44, for sending to the implantable device. It is the function of the transmitting network 56 to convert the command word generated by the driver circuit 54 into a form suitable for transmission to the implantable device 32, i.e., to generate a carrier signal that is modulated with the command word, and to present the modulated carrier signal to an antenna coil 57.

As shown in FIG. 2, the transmitting network 56 includes a plurality of individual transmitting circuits 58a, 58b, ... 58n. A switch 60, controlled by the microprocessor 44, determines which of the individual transmitting circuits 58a, 58b, ... 58n receives the command word from the driver circuit 54. The selected transmitter circuit then presents the carrier signal modulated with the command word to the antenna coil 58. It is noted that while FIG. 2 shows that a single antenna coil 57 is shared by all of the individual transmitting circuits 58a, 58b, ... 58n, it would also be possible for one of more of the individual transmitter circuits to have its own antenna coil.

The purpose of having a plurality of individual transmitting circuits 58a, 58b, ... 58n within the transmitting module 56 is to allow the external device 30 to be used with a wide variety of different types implantable devices 32. Such implantable devices may use entirely different schemes for establishing a telemetry link. For example, one type of implantable device may use reflected impedance as the mechanism for establishing a communication link between it and an external programmer. Another type of implantable device may use an RF (radio frequency) link. Sill another type may use magnetic coupling. Further, the type of modulation that is used may also vary widely from implantable device to implantable device. For example, some implantable devices may use FSK (frequency shift keying) modulation, while others may use ASK (amplitude shift keying) or PSK (phase shift keying) modulation. See, e.g., U.S. Pat. No. 4,681,111. Hence, each individual transmitter circuit 58a, 58b, ... 58n is designed to interface with one particular type of implantable device, i.e., to provide the right type of modulation at the right carrier frequencies according to the right mode of transmission for the particular implantable device with which a communication link is to be established.

As further shown in FIG. 2, the external device 30 further includes a receiver network 62. It is the function of the receiver network 62 to receive a signal 42 sent from the implantable device 32 through a receiving antenna coil 64. The receiving network 62, like the transmitting network 56, includes a plurality of individual receiving circuits 66a, 66b, ... 66n, one of which is selected to receive the signal 42 by a switch 68 controlled by the microprocessor 44. Each receiving circuit 66a, 66b, ... 66n is designed to be compatible with the type of signal 42 sent from a particular type of implantable device. Thus, regardless of whether the implantable device sends a signal 42 that is modulated using PSK, FSK, or ASK (or any other type of modulation), and regardless of whether the mode of transmission is reflected impedance, RF telemetry, or any other form of transmission, one of the receiver circuits 66a, 66b, ... 66n can be selected by the microprocessor 44 to properly receive the signal. In this manner, the external device 30 can be a truly universal external device that can interface with a large number of different types of implantable devices.

As will be evident to those skilled in the art, while FIG. 2 shows individual blocks for the respective transmitter circuits 58a, 58b, 58n and the respective receiving circuits 66a, 66b, ... 66n, many of the components of these circuits, including the antenna coils 57 and 64, may be shared between the various circuits. Further, the switches 60 and 68 are intended as functional switches. In practice, actual switches may not be necessary; rather different portions of the transmitting network 56 or receiving network 62 may be simply enabled or disabled by the microprocessor 44 in order to achieve the desired compatibility with the particular implantable device being used. Detailed schematic diagrams of suitable transmitting circuits and receiving circuits for use within the transmitting network 56 and the receiving network may be readily fashioned by those skilled in the art, or obtained from the previously cited patents.

Still referring to FIG. 2, it is seen that the output signal from the receiving network 62, typically a modulated IF (intermediate frequency) signal of some type, is directed to a filter circuit 70 over signal line 69. The purpose of the filter circuit 70 is to filter out noise from the received signal. Said another way, the purpose of the filter circuit 70 is to accept only a narrow band of frequencies centered around the expected frequency of the received signal, thereby significantly improving the signal-to-noise ratio of the filtered signal appearing on signal line 72 (output of the filter 70). Typically, the filter 70 comprises a bandpass filter (BPF) centered about the frequency of interest.

The output of the filter 70, i.e., the signal appearing on signal line 72, is next directed to a demodulator circuit 74. It is the function of the demodulator circuit 74 to demodulate the filtered signal, thereby recovering the data included in the original signal 42 sent by the implantable device 32. Typically, the demodulator 74 comprises an AM demodulator, as the receiver network 62 is designed to convert whatever type of modulation is used to an IF signal that is amplitude modulated (AM). The recovered data from the demodulator 74 appears on signal line 76 (the output line(s) of the demodulator 74) as a DATA signal. This DATA signal is then made available to other circuits within the external device for display, storage, or other uses.

One of the uses that may be made of the DATA signal recovered from the demodulator 74 is to signal the microprocessor 44 that certain events have occurred, or have not occurred, within the implantable device 32, i.e., to indicate to the microprocessor 44 the current status of the implantable device 32. The current status of the implantable device, as well as the current status of the external device, as indicated by one or more STATUS signals 80, controls the next sequence of instructions to be followed by the microprocessor. To this end, the DATA signal is directed to a multiplexer circuit 78, as are the STATUS signals 80. The multiplexer circuit 78 selects one of the signals presented thereto, i.e., the DATA signal on signal line 76 or one of the STATUS signals 80, and presents the selected signal to an analog-to-digital converter (ADC) 82. The ADC 82 converts the selected signal, which is an analog signal, to a corresponding digital signal, and presents the digital signal to the microprocessor 44. The microprocessor 44 then examines the received signal and takes appropriate action depending upon the value thereof.

Referring next to FIG. 3, a block diagram of an external programming device 30' is shown that includes the self-test means of the present invention. Most of the blocks shown in FIG. 3 correspond to blocks of FIG. 2, and are identified by the same reference number. FIG. 3, however, includes a first summing circuit 84 interposed between the driver circuit 54 and the transmitter network 56. This summing circuit 84 allows a signal from the microprocessor 44, received over signal line 88, to be injected into (added to) the command signal that is presented to the transmitter network 56. A second summing circuit 86 is interposed between the receiving network 62 and the filter 70. This summing circuit 86 allows a signal from the microprocessor 44, received over signal line 90, to be selectively injected into (added to) the data signal received by the receiver network 62. Further, a switch S1 is inserted between the filter 70 and the demodulator 74. This switch, which is controlled by the microprocessor 44, allows either the filtered signal from the filter circuit 70, or the modulated carrier signal presented to the antenna coil 57 by the transmitter network 56, to be presented as an input signal to the demodulator circuit 74. An attenuator circuit 92 attenuates the modulated carrier signal from the transmitter network 56 prior to connecting it to the switch S1.

The summing circuits 84 and 86 may be realized using a simple resistive summing network, or equivalent, as shown in FIG. 4. Such a network provides a controlled gain constant for each signal summed therein. This gain constant may be controlled by the value of the resistors used therein. As shown in FIG. 4, for example, a first resistor 94 has a value R, and a second resistor 96 has a value kR. When the relative magnitude of the signal applied to the free end of resistor R has a value of 1, and the relative magnitude of the signal applied to the free end of resistor kR has a value of 1/k, both signals are summed equally, i.e., the output signal, at the common end of resistors R and kR, includes 50% of one signal and 50% of the other signal.

The configuration shown in FIG. 3 advantageously allows numerous self-tests to be performed within the external device 30'. For example, if the transmitting portion of the device 30' is to be tested, the microprocessor 44 generates an appropriate test command word, which may simply be a square wave at a known frequency. This test command word is then injected into the summing network 84. The driver circuit 54 may be disabled by the microprocessor during this time, so that the test command signal is the only signal presented to the transmitter network 56. The transmitter network 56 modulates a carrier signal with the test command word and presents the resulting output signal to the antenna coil 57. An attenuated version of this same output signal is presented to switch S1, where it is selected and presented to the input of the demodulator circuit 74. The demodulator circuit 74 demodulates the signal to remove the carrier therefrom, and presents the resulting demodulated test command word back to the microprocessor 44 by way of the multiplexer 78 and the ADC 82. The microprocessor 44 compares the test command word thus received with the test command word generated. If the test command word received is the same as the test command word generated, then this particular test, directed to testing the transmitting portion of the external device 30', is deemed to have been successfully passed.

Many other self-tests can be performed with the configuration shown in FIG. 3. For example, an appropriate test signal can be generated within the microprocessor 44 and injected into the summing circuit 86. This signal is then passed through the filter 70 and selected by switch S1 for presentation to the demodulator circuit 74. The output of the demodulator circuit 74 may then be coupled back to the microprocessor through the multiplexer 78 and ADC 82 and compared against an expected result, thereby testing the performance of the filter 70 and the demodulator 74. For example, by varying the frequency of the test signal injected into the summing network 86, the frequency response of the filter 70 can be accurately determined. The test signal 90 is a SQW (square wave), however, the bandpass filter will usually select the fundamental, and reject the harmonic, so it is not necessary to generate a sine wave. Alternatively, the output of the demodulator circuit 74 may be passed to other portions of the external device 30', causing one or more of the STATUS signals 80 to change. The appropriate STATUS signals can then be selected by the multiplexer 78 and directed back to the microprocessor 44 by way of the ADC 82 in order to verify that a proper status has been achieved. In this way, numerous functions within the external programming device may be tested.

Further, additional tests of the circuits of the external programming device are made possible by performing the self-tests while a known good implantable device is positioned next to the transmitting antenna 57 and the receiving antenna 64. For example, using such a configuration (known good implantable device next to antenna 57), a test command can be generated as described above. However, instead of selecting the carrier-modulated version of this test command for presentation to the demodulator 74 with switch S1, switch S1 selects the output of the filter 70. The test command thus passes to the implantable device, causing the implantable device to assume a particular operating mode. This operating mode is indicated in data signals returned to antenna 64, which data signals are processed through the receiver network 62, filter 70, and demodulator 74. The output of the demodulator 74 may then be coupled back directly to the microprocessor 44 through the multiplexer 78 and ADC 82, or indirectly through testing the response of the external device 30' to the output of the demodulator 74 as indicated by selected STATUS signals 80.

Tests may also be performed using the configuration shown in FIG. 3 in order to test an implantable device, such as on the assembly line where the implantable devices are fabricated. In such a case, the external device would be tested first, e.g., using the techniques described above, and then the external device would be used to test the response of implantable devices to a sequence of test commands.

Figure 5:
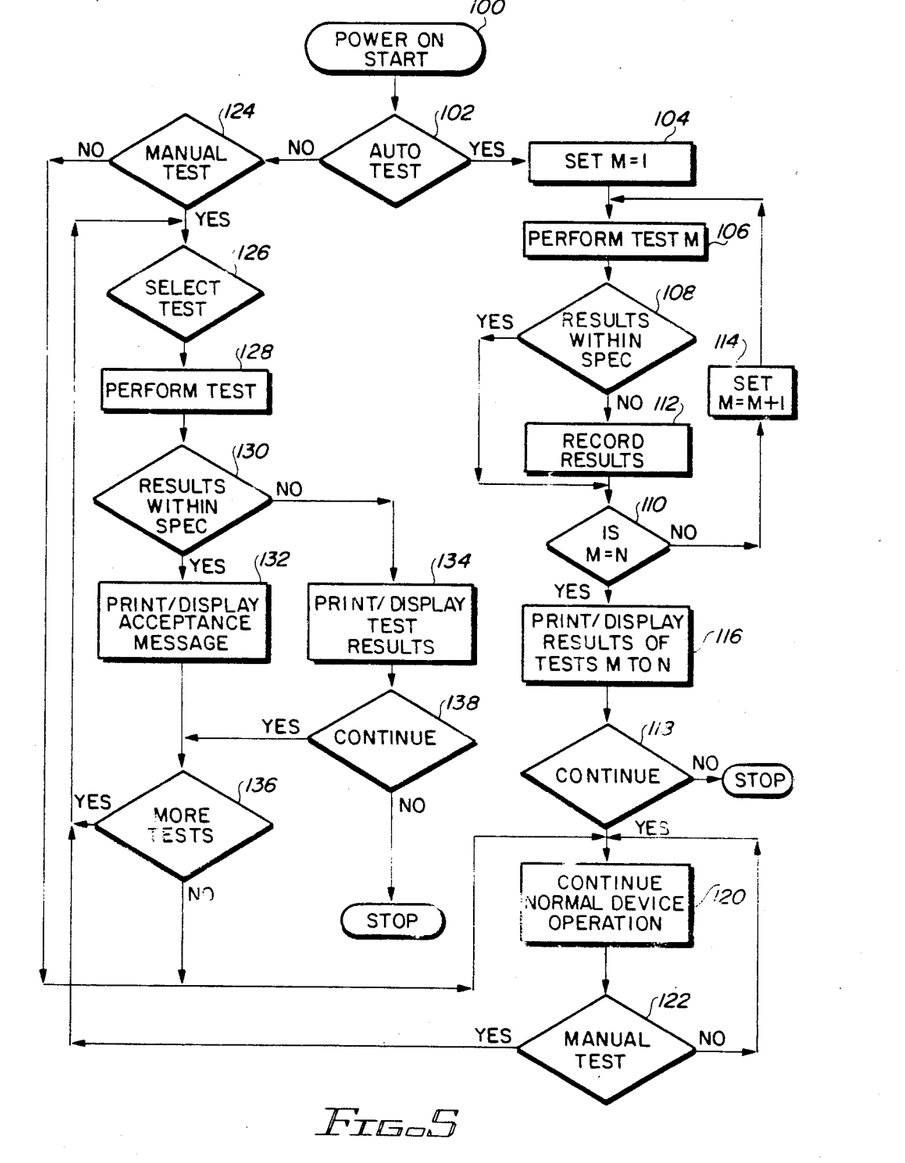
FIG. 5 is a flow chart illustrating one manner in which the self-test means of the present invention carries out its testing function.

In a preferred embodiment, the external device 30' may selectively invoke a sequence of self-tests automatically when the external device is first powered on. Such is achieved by programming the microprocessor to follow a sequence of instructions as depicted in the flow chart of FIG. 5. In FIG. 5, for example, it is seen that when power is first applied to the device (block 100 in FIG. 5), a decision is made (decision block 102) as to whether the self-tests are to be automatically invoked. If so, an appropriate indicator is set to a first value (block 104), identifying the first test that is to be performed. This first test is performed (block 106), and the results of the test are then compared against results that should have been obtained (block 108) to determine whether or not the test was passed. If the test was passed, then a determination is made as to whether all the tests that are to be automatically performed have been performed (block 110). If a particular test was not passed, then the test results of such test are recorded (block 112) before the determination is made as to whether any additional test are to be performed (block 110). If additional tests are to be performed, then the indicator is incremented to the next value (block 114), identifying the next test that is to be performed. This next test is then performed and the process repeats itself as described above, with all the tests in the test sequence being performed in order and with the test results being recorded or saved only when the test results are not within specification.

When all the tests have been performed, the test results from those tests that did not pass are printed or displayed (block 116). If all the tests passed, then no test results are displayed. Hence, the absence of any test results being displayed provides an indication to the operator that all the tests passed, and that normal operation of the eternal device can continue (block 120), if the operator so selects (block 118). If one or more tests did not pass, the operator is given an opportunity to review the displayed test results and make a decision (block 118) as to whether the external device should continue to be used or whether corrective action should be taken.

In addition to the automatic tests described above, the operator may also select a particular manual test that he or she wants to perform. If a manual test is selected, either at power turn-on (block 124) or during normal device operation (block 122), the operator manually selects the particular test that is to be performed (block 126). The selected test is then performed (block 128), and a determination is made (block 130) by the microprocessor as to whether the test results are within specification. If so, an appropriate message is displayed (block 132) indicating that the selected test was passed successfully, and the operator is asked whether any additional tests are to be performed (block 136). If an additional test is to be performed, that test is selected (block 126), and the process repeats as described above. If additional tests are not to be performed, the normal operation of the external device continues (block 120).

If the selected test is not passed, i.e., if the test results of the selected test are not within specification (block 130), then an appropriate message is displayed that the test was not passed and the test results are printed and/or displayed (block 134) for review by the operator. With the failed test results being displayed, the operator is given an opportunity to decide whether to continue use of the external device (block 138). If so, additional tests may be performed (block 136) prior to returning the external device to normal (non-text mode) operation (block 120).

Table 1 (below) details some thirty different tests that may be performed by an external programming device 30' configured as shown in FIG. 3. These tests are not meant to be limiting, but are only exemplary of the many and varied tests that may be performed using the self-test configuration of the present invention. Those skilled in the art may readily devise additional tests that could easily be performed using the present invention. Indeed, one of the advantages of the present invention is its versatility and adaptability.

It is submitted that those skilled in the electronic arts can readily fashion an external programming device having the self-test and other circuits described herein in order to practice the invention. A preferred device for the microprocessor 44, for example, is the commercially available Intel 87451 microprocessor chip. The multiplexer 78 may be realized using a CMOS CD4051, or equivalent device. The ADC 82 may be realized using a TLC549 analog-to-digital converter. The attenuator circuit 92 may be realized using two resistors in a conventional voltage dividing network. The switch S1 may be realized using any of numerous commercially available solid-state switches, such as the CD4053 or the DG2212. All of these commercially available devices are fully described in the literature.

While the invention described herein has been described with reference to a particular embodiment and application thereof, numerous variations and modifications could be made thereto by those skilled in the art without departing from the spirit and scope of the invention as claimed.

What is claimed is:

1. In a communication system having driver means for generating a first signal that is to be transmitted; transmitter means for presenting said first signal to antenna means as an output signal; control means for controlling said driver means; receiver means for receiving an input signal and converting the same to a second signal; filter means for filtering said second signal and for producing a filtered second signal therefrom; demodulation means for demodulating said filtered second signal and for producing a demodulated signal therefrom; and first switch means for selectively connecting one of a plurality of status signals, including said demodulated signal, to said control means; self test means for testing the operation of said system comprising:

signal generating means within said control means for generating a test signal;

first summing means for selectively adding said test signal to said first signal, whereby said output signal may selectively include said test signal;

second summing means for selectively adding said test signal to said second signal, whereby said filtered second signal may selectively include said test signal; and second switch means for selectively connecting one of said output signal or said filtered second signal to said demodulation means, whereby one of said status signals connected to said control means may selectively include said test signal after said test signal has passed through said transmitter means and demodulator means or after said test signal has passed through said filter means and demodulation means;

said control means including means for checking the selected one of said status signals returned thereto to verify that said test signal produced an anticipated response in the performance of said communication system.

2. The self-test means set forth in claim wherein said signal generating means includes means for automatically generating said test signal at prescribed times during the operation of said communication system, said self-test means automatically performing its function of checking selected ones of said status signals at said prescribed times.

3. The self-test means set forth in claim 2 wherein said signal generating means automatically generates said test signal immediately after the application of power to said communication system, whereby the self-test means performs its testing function when power is first applied to the communication system.

4. The self-test means set forth in claim 2 wherein said signal generating means generates a sequence of test signals, each being added in sequence to a selected one of said first and second summing means, said control means including means for controlling said first and second switch means in a corresponding sequence, said first switch means being controlled to select an appropriate status signal for return to said control means as a function of the particular test signal generated, said second switch means being controlled to select an appropriate signal to connect to said demodulation means depending upon whether the particular test signal generated is added to said first or second summing means, and the checking means of said control means including means for checking the returned status signals corresponding to each test signal generated in order to determine if each test signal produced an anticipated response of the communication system, whereby said self-test means automatically and sequentially tests a plurality of functions of said communication system.

5. The self-test means set forth in claim 4 wherein said checking means of said control means includes means for recording the response obtained from each test signal when said response is not an anticipated response.

6. The self-test means set forth in claim further including means for attenuating the output signal applied to said second switch means from said transmitter means by a prescribed amount.

7. The self-test means set forth in claim wherein said control means comprises a microprocessor, and wherein said signal generating means within said control means includes a stored sequence of instructions that causes said microprocessor to generate said test signal and apply it to at least one of said first or second summing means at an appropriate time during the operation of said communication system.

8. The self-test means set forth in claim 7 wherein said stored sequence of instructions causes said microprocessor to generate said test signal as manually initiated by an operator of said communication system.

9. The self-test means set forth in claim 7 wherein said stored sequence of instructions causes said microprocessor to automatically generate said test signal at prescribed times during the operation of said communication system.

10. The self-test means set forth in claim 7 wherein said transmitter means and said receiver means each include means for selectively interfacing with a plurality of different types of implantable devices.

11. The self-test means set forth in claim 10 wherein said different types of implantable devices comprise different models of pacemakers.

12. The self-test means set forth in claim 7 wherein said status signals selected by said first switch means comprise analog signals, and said communication system further includes analog-to-digital converter means interposed between said first switch means and said microprocessor for converting the selected one of said status signals to a digital signal prior to returning said signal to said microprocessor.

13. A communication system comprising:
  driver means for generating a first signal that is to be transmitted;
  transmitter means for presenting said first signal to antenna means as an output signal;
  control means for controlling said driver means;
  receiver means for receiving an input signal and for converting the same to a second signal;
  filter means for filtering said second signal and for producing a filtered second signal therefrom;
  demodulation means for demodulating said filtered second signal and for producing a demodulated signal therefrom;
  first switch means for selectively connecting one of a plurality of status signals, including said demodulated signal, to said control means; and
  self-test means for testing the operation of said system, said self-test means including:
    signal generating means within said control means for generating a test signal,
    first summing means for selectively adding said test signal to said first signal, whereby said output signal may selectively include said test signal,
    second summing means for selectively adding said test signal to said second signal, whereby said filtered second signal may selectively include said test signal, and
    second switch means for selectively connecting one of said output signal or said filtered second signal to said demodulation means, whereby one of said status signals connected to said control means may selectively include said test signal after said test signal has passed through said transmitter means and demodulator means or after said test signal has passed through said filter means and demodulation means;
  said control means including means for checking the selected one of said status signals returned thereto to verify that said test signal produced an anticipated effect on the performance of said communication system.

14. A system for testing an external programming device, said external programming device being adapted to communicate with an implantable device, said system including:
  test signal means for generating a test signal within said external programming device;
  injection means for injecting said test signal into prescribed circuit locations within said external programming device,
  monitoring means for monitoring prescribed signals, resulting from the injecting of said test signal, at prescribed circuit locations within said external programming device, and
  comparison means for comparing the value of various parameters associated with the monitored signals with expected parameter values.

15. The system of claim 14 wherein said external programming device includes a microprocessor for controlling its operation, and wherein said means for generating a test signal includes means coupled to said microprocessor for causing said microprocessor to automatically generate said test signal at prescribed times during its operation.

16. The system of claim 14 wherein said external programming device includes means for automatically generating said test signal at the time said programming device is first powered on.

17. The system of claim 14 wherein said test signal generating means includes means for generating a plurality of test signals; said injection means includes means for injecting each of said test signals into prescribed circuit locations; said monitoring means includes means for monitoring prescribed signals, resulting from the injecting of said test signals, at prescribed circuit locations within said external programming device; and said comparison means includes means for comparing the value of various parameters associated with each of the monitored signals with expected parameter values, a plurality of functions of said external programming device being tested by said plurality of test signals.

18. The system of claim 17 wherein said test signal generating means includes means for generating said plurality of test signals in a prescribed sequence; said injection means includes means for injecting each of said test signals in said prescribed sequence into prescribed circuit locations; said monitoring means includes means for monitoring, in sequence, the prescribed signals resulting from the injecting of said test signals at the prescribed circuit locations within said external programming device; and said comparison means includes means for comparing, in sequence, the value of various parameters associated with each of the monitored signals with expected parameter values, a plurality of tests thereby being performed in said prescribed sequence, each of said tests testing a separate function of said external programming device.

19. The system of claim 18 further including means for automatically performing said plurality of tests in said prescribed sequence.

20. A method of automatically testing an external programming device adapted for use with an implantable device, said method comprising the steps of:
(a) automatically performing a prescribed test at the time said external programming device is first powered on;
(b) determining if the results of the test performed in step (a) are within a range of acceptable results;
(c) automatically saving the results of the test performed in step (a) if the results of the test are not within the range of acceptable results as determined in step (b);
(d) automatically repeating steps (a) through (c) for additional prescribed tests, if any, that are to be performed, with each additional test being initiated at the conclusion of the preceding test; and
(e) automatically displaying the results of the tests saved in step (c) for all the prescribed tests that are performed;
whereby a sequence of prescribed tests are automatically performed when the programming device is first powered on, with the results of any test not within an acceptable range of results being automatically displayed.

21. The method as set forth in claim 20 wherein at least one of the prescribed tests performed as part of said sequence of prescribed tests includes:
generating a test signal within said external programming device,
injecting said test signal into prescribed circuit locations within said external programming device,
monitoring prescribed signals, resulting from the injecting of said test signal, at prescribed circuit locations within said external programming device, and
comparing the value of various parameters associated with the monitored signals with expected parameter values.

22. The method as set forth in claim 20 wherein each of the prescribed tests performed as part of said sequence of prescribed tests includes:
generating a test signal within said external programming device,
injecting said test signal into prescribed circuit locations within said external programming device,
monitoring prescribed signals, resulting from the injecting of said test signal, at prescribed circuit locations within said external programming device, and
comparing the value of various parameters associated with the monitored signals with expected parameter values.

23. A method for testing an external programming device, said external programming device being adapted to communicate with an implantable device, said method comprising the steps of:
(a) generating a test signal within said external programming device;
(b) injecting said test signal into prescribed circuit locations within said external programming device,
(c) monitoring prescribed signals, resulting from the injecting of said test signal, at prescribed circuit locations within said external programming device, and
(d) comparing the value of various parameters associated with the monitored signals with expected parameter values.

24. The method of claim 23 wherein said external programming device includes a microprocessor for controlling its operation, and wherein step (a) includes programming said microprocessor to automatically generate said test signal at prescribed times during its operation.

25. The method of claim 23 wherein said external programming device includes means for automatically generating said test signal at the time said programming device is first powered on.

26. The method of claim 23 wherein step (a) includes generating a plurality of test signals; step (b) includes injecting each of said test signals into prescribed circuit locations; step (c) includes monitoring prescribed signals, resulting from the injecting of said test signals, at prescribed circuit locations within said external programming device; and step (d) includes comparing the value of various parameters associated with each of the monitored signals with expected parameter values, a plurality of functions of said external programming device being tested by said plurality of test signals.

27. The method of claim 26 wherein step (a) includes generating said plurality of test signals in a prescribed sequence; step (b) includes injecting each of said test signals in said prescribed sequence into the prescribed circuit locations; step (c) includes monitoring, in sequence, the prescribed signals resulting from the injecting of said test signals at the prescribed circuit locations within said external programming device; and step (d) includes comparing, in sequence, the value of various parameters associated with each of the monitored signals with expected parameter values, a plurality of tests thereby being performed in said prescribed sequence, each of said tests testing a separate function of said external programming device.

28. The method of claim 27 further including performing said plurality of tests in said prescribed sequence automatically.

29. A method of testing an external programming device adapted for use with an implantable device, said external programming device including various circuits that, when functioning properly, establish a telemetry link with the implantable device over which commands may be sent to the implantable device and data may be received from the implantable device, said method comprising the steps of:

generating a suitable test signal, injecting the test signal into appropriate locations within the circuits of the programming device so that the test signal is coupled to the input of a particular circuit to be tested, routing the resulting signal, obtained or derived from the output of the particular circuit to be tested, back to a central location, and comparing the resulting signal routed back to the central location against a standard signal that would be received at the central location if the particular circuit to be tested is functioning properly.

* * * * *

UNITED STATES PATENT AND TRADEMARK OFFICE
CERTIFICATE OF CORRECTION

PATENT NO. : 4,979,506
DATED : December 25, 1990
INVENTOR(S) : Sergiu Silvian

It is certified that error appears in the above—identified patent and that said Letters Patent is hereby corrected as shown below:

Col. 13, line 68, after "adaptability." add

-- TABLE 1

| TEST # | NAME | NOTES |
|---|---|---|
| 1 | Power supply lines | |
| 2 | Sw-mode PS Frequency | |
| 3 A,B | FVC test | DC response |
| 4 A,B,C | XMTR off Vc | |
| 5 A,B,C | PLT xmtr | w, and w/o magnet |
| 5 D | PLT xmtr | xmtr rise time |
| 6 A,B,C | AFP-L xmtr | Vc, xmtr, freq |
| 6 D,E,F | AFP-H xmtr | Vc, xmtr, freq |
| 7 A,B | RI Filter & Absolute Value Detector | |
| 8 | Zero-crossing/Low Freq. Det. | |
| 9 A,B,C | PLT receiver Settling Time | BASLN,AMPL,FVC2 |
| 10 A,B,C | AFP-L FSK receiver Settling Time | BASLN,AMPL,FVC2 |
| 11 A,B,C | AFP-H FSK receiver Settling Time | BASLN,AMPL,FVC2 |
| 12 A,B,C | AFP-L PSK receiver Settling Time | BASLN,AMPL,FVC2 |
| 13 A,B,C | AFP-H PSK receiver Settling Time | BASLN,AMPL,FVC2 |
| 14 | FVC and FILTER | delay and rise time |
| 15 A-G | FSK Receiver Freq. Response | |

UNITED STATES PATENT AND TRADEMARK OFFICE
CERTIFICATE OF CORRECTION

PATENT NO. : 4,979,506
DATED : December 25, 1990
INVENTOR(S) : Sergiu Silvian

It is certified that error appears in the above—identified patent and that said Letters Patent is hereby corrected as shown below:

| | | |
|---|---|---|
| 16 A-G | PSK Receiver Freq. Response | |
| 17 A,B | Analog outputs and LED | |
| 18 | 64k memory test | |
| 19-20 | | reserved |
| 21 A,B | Active 2k/8k XMTR | |
| 22 A,B | 2k Receiver Transients and Noise | |
| 23 A-F | 2k Receiver Freq. Response | |
| 24 A,B | 8k Receiver Transients and Noise | |
| 25 A-F | 8k Receiver Freq. Response | |
| 26 | 2k Async. Demodulator | |
| 27 | 8k Sync. Demodulator | |
| 28 | PLL Acquisition Time | |
| 29 | 8k Receiver, Ext. Xmtr. | pacer stimulator |
| 30 | MTM Current Consumption | |

UNITED STATES PATENT AND TRADEMARK OFFICE
CERTIFICATE OF CORRECTION

PATENT NO. : 4,979,506

DATED : December 25, 1990

INVENTOR(S) : Sergiu Silvian

It is certified that error appears in the above-identified patent and that said Letters Patent is hereby corrected as shown below:

Claim 2, Col. 14, line 60, "claim" should be --claim 1--.

Claim 6, Col. 15, line 30, "claim" should be --claim 1--.

Claim 7, Col. 15, line 34, "claim" should be --claim 1--.

Signed and Sealed this

Twenty-fourth Day of November, 1992

Attest:

DOUGLAS B. COMER

*Attesting Officer*  *Acting Commissioner of Patents and Trademarks*